(12) United States Patent
Desponds

(10) Patent No.: US 10,238,358 B2
(45) Date of Patent: Mar. 26, 2019

(54) SYSTEMS AND METHODS OF RADIATION DOSE MAPPING

(71) Applicant: General Electric Company, Schenectady, NY (US)

(72) Inventor: Lionel Francois Desponds, Buc (FR)

(73) Assignee: General Electric Company, Schenectady, NY (US)

( * ) Notice: Subject to any disclaimer, the term of this patent is extended or adjusted under 35 U.S.C. 154(b) by 265 days.

(21) Appl. No.: 15/386,717

(22) Filed: Dec. 21, 2016

(65) Prior Publication Data

US 2018/0168534 A1    Jun. 21, 2018

(51) Int. Cl.
*A61B 6/00* (2006.01)
*A61B 6/04* (2006.01)
*G01T 1/02* (2006.01)

(52) U.S. Cl.
CPC .......... *A61B 6/542* (2013.01); *A61B 6/0407* (2013.01); *A61B 6/40* (2013.01); *A61B 6/4441* (2013.01); *A61B 6/461* (2013.01); *A61B 6/5211* (2013.01); *G01T 1/02* (2013.01)

(58) Field of Classification Search
CPC ......... A61B 6/542; A61B 6/0407; A61B 6/40; A61B 6/4441; A61B 6/461; A61B 6/5211; G01T 1/02
USPC ................................................... 378/65, 165
See application file for complete search history.

(56) References Cited

U.S. PATENT DOCUMENTS

| 9,095,278 B2 | 8/2015 | Desponds et al. |
| 9,138,197 B2 * | 9/2015 | Vaillant ............... A61B 6/4441 |
| 2012/0022845 A1 | 1/2012 | Bismuth et al. |

FOREIGN PATENT DOCUMENTS

WO    2004070420 A2    8/2004

OTHER PUBLICATIONS

Balter et al., "Fluoroscopically Guided Interventional Procedures: A Review of Radiation Effects on Patients' Skin and Hair", Radiology, Feb. 2010, vol. 25, No. 2.
Bordier et al., "Patient Dose Map Indications on Interventional X-Ray Systems and Validation with Gafchromic XR-RV3 Film", Radiation Protection Dosimetry, 2015, vol. 163, No. 3, pp. 306-318.
Oines, et al., "Alignment of the Patient Graphic Model Using Fluoroscopic Iamges for Skin Dose Mapping", 2016.
Omar et al., "Monte Carlo Investigation of Backscatter Factors for Skin Dose Determination in Interventional Neuroradiology Procedures", Medical Imaging, 2014.

(Continued)

*Primary Examiner* — Courtney D Thomas
(74) *Attorney, Agent, or Firm* — Andrus Intellectual Property Law, LLP

(57) ABSTRACT

Systems and methods of estimating radiation dose include obtaining at least one radiation exposure value from a location marked on a patient model. A radiation exposure of the patient is estimated using a dose model which includes the patient model. At least one correction factor is calculated based upon the radiation exposure value and the estimation of radiation exposure using the dose model. The at least one correction factor is applied to the dose model and a refined estimation of radiation exposure is produced based upon the at least one correction factor and the dose model.

20 Claims, 6 Drawing Sheets

(56) References Cited

OTHER PUBLICATIONS

Rana et al., "A tracking system to calculate patient skin dose in real-time during neurointerventional procedures using a biplane x-ray imaging system", Medical Physics, 2016.
Safari et al., "Characterization of a MOSkin detector for in vivo skin dose measurements during interventional radiology procedures", Medical Physics, 2015.
Speidel et al., "Comparison of entrance exposure and signal-to-noise ratio between an SBDX prototype and a wide-beam cardiac angiographic system", Medical Physics, 2006.
Suzuki et al., "Radiosensitive Functional Dye: Clinical Application for Estimation of Patient Skin Dose", Radiology, May 2006, vol. 239.
"Radiation Dose Management for Fluoroscopically-Guided Interventional Medical Procedures", by National Council on Radiation Protection and Measurements, Jul. 21, 2010.
"Visual Evaluation of the Surface Peak Skin Dose with GAFCHROMIC® XR-RV3 Dosimetry Film", by International Specialty Products, 2009.

\* cited by examiner

SYSTEMS AND METHODS OF RADIATION DOSE MAPPING

BACKGROUND

Embodiments of the present invention relate to the field of medical imaging using radiation and more particularly, related to the estimation and monitoring of radiation doses to which a body or some organs thereof are subjected, when acquiring images by means of a radiation imaging system.

Exposure of a patient to X-rays produces two types of effects: stochastic, long-term effects (cancer risk) are related to the dose accumulated by patients throughout their lifetime, from this perspective, any radiation dose must be weighed against the benefit for the patient, and short-term effects over the hours, days and weeks following after exposure (burns), these are related to short-time exposure at very high dose.

Yet, radiation imaging can expose a patient's body or some parts thereof to radiation doses which may vary substantially from one acquisition to another, particularly in relation to the chosen directions of exposure.

Also, radiation and notably X-rays interact very differently with the bones or tissues of the human body, preventing easy understanding of the level of radiation to which a given part of the body can still be exposed.

There is therefore a need for the monitoring of radiation doses received by a body or by different parts thereof during an examination involving one or more acquisitions of radiological images.

It is also desired, when acquiring new images, to avoid accumulating too excessive radiation doses in some body regions or in some organs, and hence to be able to determine the acquisition conditions for subsequent images allowing optimization of the radiation doses accumulated in a body.

Fluoroscopy uses a continuous or series of pulsed X-ray beam used to image movement of organs and objects within the body. Fluoroscopically guided minimally invasive procedures have become common due to generally lower trauma and faster recovery compared to conventional surgery. Examples of Fluoroscopically Guided Interventional (FGI) procedures include percutaneous transluminal coronary angioplasty and radiofrequency (RF) ablation for treatment of cardiac dysrhythmias. Interventional procedures are often made in several exam sessions that are generally made within a period during which healing effects cannot be fully completed. In such case, the overall risk estimation can be a conservative cumulation of dose across these sessions. From one session to the next, patients are only approximately repositioned to the same location, so that the X-ray beam projections are not the same in all sessions and this leads to inaccuracy in dose estimation when these differences are not fully considered.

Methods are known to estimate the distribution of radiation doses accumulated in a patient's body. Radiation dose may be estimated by direct measurement using dosimeters located on the patient. Radiation reactive sheets of material provide resolution, but do not conform to the patient's body. Point dosimeters can be located on a patient, but are known to under sample radiation dose and have low sampling resolution. Mathematical models can be used to estimate radiation dose, but do have limited accuracy to account for patient size and location or radiation backscatter and therefore limited accuracy to cumulate patient dose across multiple exam sessions.

BRIEF DISCLOSURE

An exemplary embodiment of a system for estimation of radiation dose of a medical imaging system includes a dosimeter adapted to be associated with a patient. An X-ray source is configured to generate an X-ray beam in an imaging procedure in the direction of the dosimeters. A processing unit obtains at least one dose model. The dose model includes a patient model. The processing unit receives at least one radiation exposure value from the dosimeter. The processing unit marks a location of the dosimeter on the patient model and estimates the radiation exposure of the patient during the imaging procedure according to the dose model. The processing unit calculates at least one correction value based upon the estimated radiation exposure of the patient according to the dose model and the at least one radiation exposure value received from the dosimeter. The processing unit applies the at least one correction factor to the dose model and produces a refined estimation of radiation exposure of the patient based upon the at least correction factor and the dose model a graphical display is operated by the processing unit to visually present a refined estimation of the radiation exposure of the patient.

An exemplary embodiment of a method of estimating radiation dose includes obtaining a patient model. A location of at least one radiation exposure value measurement is marked on the patient model. At least one radiation exposure value from a radiation exposure event is obtained at a processor. A radiation exposure of the patient during the radiation exposure event is estimated with a dose model which includes the patient model to produce at least one dose model value. At least one correction value is calculated based upon the at least one radiation exposure value and the at least one dose model value. At least one correction factor is applied to the dose model. A radiation exposure of the patient is estimated based upon the at least one correction factor and the dose model.

DETAILED DISCLOSURE

Figure 1:
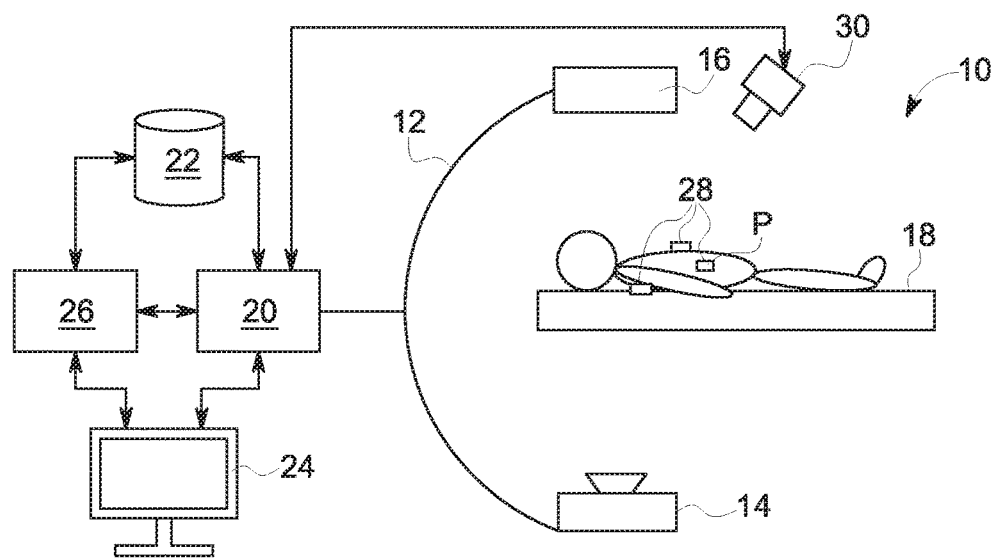
FIG. 1 is a system diagram of an exemplary embodiment of a medical imaging system.

FIG. 1 depicts an exemplary embodiment of a medical imaging system 10 with a C-arm 12 used for examining a patient P. The medical imaging system 10 includes a C-arm 12 on which an X-ray source 14 and a detector 16 are arranged facing one another.

The medical imaging system 10 may include a tabletop 18 intended to receive an object to be imaged e.g. a patient P. In an exemplary embodiment, the tabletop 18 may be movable relative to the C-arm 12 in order to position the patient for imaging by the medical imaging system 10.

The detector 16 may exemplarily be a semiconductor image sensor comprising caesium iodide phosphor (scintillator) for example on a transistor/photodiode array in amorphous silicon. Other suitable detectors may include, but are not limited to a CCD sensor, a direct digital detector which directly converts X-rays into digital signals, or a detector with image enhancer. The detector 16 illustrated in FIG. 1 is exemplarily planar and defines a planar image surface, however other geometries are possible. It will be recognized that other configurations of medical imaging devices may be included within the scope of the present disclosure. Such other configurations may include, but are not limited to, configurations in which the detector is independently movable apart from the X-ray source 14. Still further exemplary embodiments include those in which the detector 16 is separate from the C-arm 12.

The medical imaging system 10 includes a control unit 20 communicatively connected to the C-arm, X-ray source 14, and the detector 16 exemplarily via wired or wireless communicative connection. The control unit 20 exemplarily includes a computer processor. The control unit 20 operates to control acquisition of medical images, for example X-ray, computed tomography, or fluoroscopy by the medical imaging system by setting parameters such as radiation dose to be emitted by the X-ray source 14 and angle position of the C-arm 12 and sending command instructions to components of the medical imaging system 10, including but not limited to the C-arm 12, X-ray source 14, and detector 16. The control unit 20 can also be used to control the positioning of the C-arm 12.

The control unit 20 may comprise a reader device (not illustrated) e.g. a diskette reader, CD-ROM, DVD-ROM reader or connection ports to read the instructions for a control or processing method from an instruction medium (not illustrated) such as a diskette, CD-ROM, DVD-ROM or USB key or in general using any removable storage medium or via a network connection. In an alternative embodiment, the control unit 20 may include or be communicatively connected to instruction medium which may be any available non-transient computer readable memory upon which the computer instructions for control or processing methods may be stored.

In an embodiment, a storage unit 22 is connected to the control unit 20 to record image parameters and medical images acquired during an imaging procedure for example. It is possible to make provision so that the storage unit 22 is located inside or outside the control unit 20. The storage unit 22 can be formed of a hard disk or SSD, or any other removable, re-write storage means (USB keys, memory cards, etc.). The storage unit 22 may be a ROM/RAM memory of the control unit 20, USB key, memory card, memory of a central server.

In an exemplary embodiment, a graphical display 24 is communicatively connected to the control unit 20 and receives instructions from the control unit 20 to operate the graphical display 24 to visually present image data from an imaging procedure performed by the medical imaging system 10. The graphical display 24 is further operable as described in further detail herein to visually present information as described in further detail herein regarding an estimated radiation dose experienced by the patient P. Methods of monitoring, estimating, and cumulating radiation dose applied to a patient being exposed or having been exposed to radiation by the medical imaging system 10 will be described in further detail herein and the graphical display 24 may be operated to present the results of such methods. The graphical display may, for example, may be a computer screen, a monitor, flat screen, plasma screen or any other type of display device of known type. The graphical display 24 may be the same as the one used to display radiological images derived from acquisition by means of the medical imaging system.

The medical imaging system 10 exemplarily further includes a processing unit 26. The processing unit 26 exemplarily performs the processing and at least partially carries out the methods of monitoring, estimating, and/or cumulating radiation dose for one or several exam sessions with retrieving past exam sessions cumulation as described in further detail herein. In exemplary embodiments the processing unit 26 may be a separate device from the control unit 20. In embodiments, the processing unit 26 may be located remotely from the rest of the medical imaging system 10 or may be implemented in a cloud based or distributed processing configuration. In still other embodiments, the processing unit 26 may be integrated with the control unit 20 and the functions of both the processing unit 26 and the control unit 20 carried out by the same hardware.

Transmission of data from the storage unit 22 to the processing unit 26 can be made via an internal or external computer network or by means of any suitable physical memory medium such as CD-ROM, DVD-ROM, external hard disk, USB key, SD card, etc. In an embodiment, the processing unit 26 is one or more computers, or one or more processors, one or more microcontrollers, one or more microcomputers, one or more programmable logic controllers, one or more application-specific integrated circuits, other programmable circuits, or other devices which include a computer such as a workstation.

As a variant, the processing unit 26 comprise a reader device (not illustrated) for example a diskette reader, CD-ROM or DVD-ROM reader, or connection ports to read and then execute the instructions of the computer executable code, software, or software modules, causing the processing unit 26 to carry out or at least partially carry out aspects of the disclosed methods and operations. The instructions may be stored on any of a variety of instruction medium (not illustrated) e.g. a diskette, CD-ROM, DVD-ROM, or USB key or more generally any computer memory medium or via a network connection.

As described in further detail herein, one or more, and in exemplary embodiments, a plurality of, dosimeters 28 are secured on or near the patient P. In exemplary embodiments, the dosimeters 28 may be analog or digital dosimeters. In one exemplary embodiment, the dosimeters may be a radiosensitive film or material. One non-limiting example of such a material is Gafchromic film, for example Gafchromic XR-RV3 film available from Ashland Specialty Ingredients, NJ, USA, although a person of ordinary skill in the art will recognize alternative materials. In another exemplary embodiment, the dosimeter is a digital dosimeter that measures the radiation exposure and reports the measured radiation exposure after completion of the imaging procedure, for example by collection of the one or more dosimeter devices and download of the radiation exposure from the device(s).

In a still further exemplary embodiment, the at least one dosimeter measures radiation exposure in real time or near real time and transmits the measurement(s) the control unit 20 and/or the processing unit 26 in real time or near real time. In exemplary embodiments, the at least one dosimeter 28 is communicatively connected to the control unit 20 and/or the processing unit 26 by a wired or wireless communicative connection. In a non-limiting embodiment, the dosimeter may report an instantaneous measurement of X-ray radiation exposure, which may be integrated by the control unit 20 and/or processing unit 26 to determine cumulative radiation dose from an imaging procedure.

As described in further detail herein, exemplary embodiments of the medical imaging system 10 may further include a camera, multiple cameras, or a set of cameras 30 for example a digital still and/or video camera. The camera or set of cameras 30 may be exemplarily communicatively connected to the control unit 20 and operate to capture images of the patient.

Figure 2:
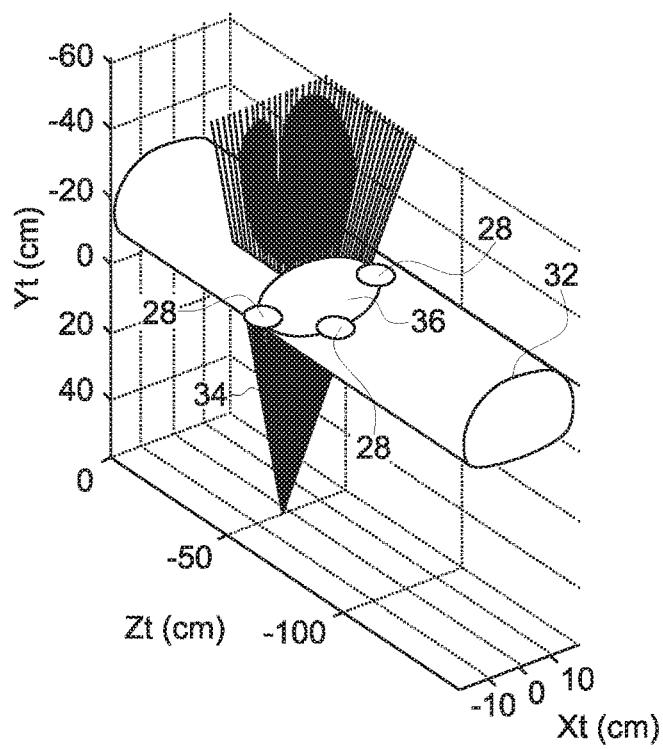
FIG. 2 graphically depicts an exemplary embodiment of a patient model.

As described above, one or more dosimeters 28, whether analog or digital are positioned on or in association with the body of the patient P. As will be described in further detail herein, exemplary embodiments of the method by which patent dose is estimated may vary or be modified in view of the number and position of the dosimeters used. In one exemplary embodiment, one or more decimeters are placed along a plane axis that contains the organ to be imaged. In one implementation of this, places one dosimeter at an anteroposterior (AP) position, which may alternatively be a posteroanterior (PA) position. Dosimeter may be positioned at a left most position and a right most position of the patient (e.g. oblique) along the same plane through the organ being imaged. FIG. 2 exemplarily depicts a patient model 32, as will be described in further detail herein. An X-ray beam 34 is shown as projecting through the patient model 32. The X-ray beam 34 is exemplarily centered on a plane 26 through the patient model 32 extending through the organ being imaged (not depicted) of the patent P. The dosimeters 28 are exemplarily arranged on the patient at location as described above and visually represented on the patient model 32 depicted in FIG. 2, exemplarily at the right side (R), left side (L), and posteroanterior (PA) position of the patient. Alignment of dosimeters on an imaging plane through the organ to be imaged helps to ensure that the dosimeters will be impinged by radiation from the X-ray beam 34 for a wide range of X-ray source 14 angulations as provided by the C-arm 12. While FIG. 2 exemplarily depicts the use of three dosimeters, it will be recognized that in alternative embodiments, more or fewer dosimeters may be used if more dosimeters are added, in some embodiments, the dosimeters may be added along the same lane 36 through the organ being imaged, while in other embodiments, dosimeters may be positioned along another plane through the organ being imaged. While FIG. 2 exemplarily depicts the use of one X-ray beam, it will be recognized that in alternative embodiments, a second X-ray beam may be used in case of a bi-plane system configuration, and alternatively more X-ray beams may be even used as e.g. in inverse geometry configuration.

Figure 3:
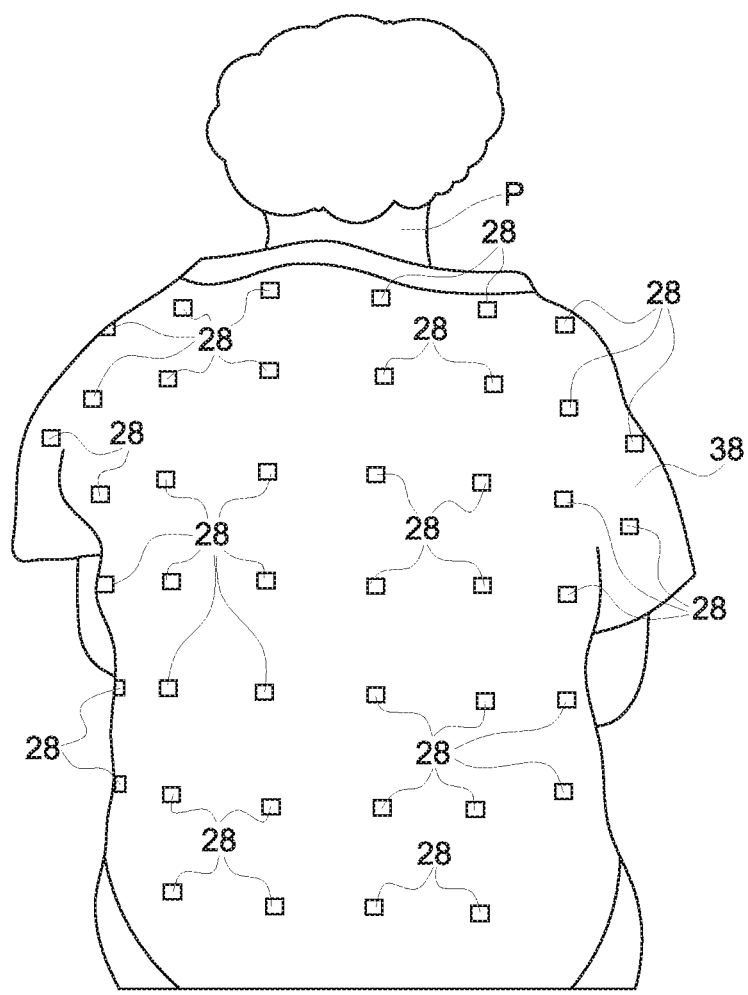
FIG. 3 depicts an exemplary embodiment in which a plurality of dosimeters are positioned in a garment.

FIG. 3 depicts an exemplary embodiment in which a plurality of dosimeters 28 are positioned on a garment 38 worn by a patient P. The garment 38 may exemplarily be a jacket, a shirt, or a gown, although this will not be limiting on the scope garments 38 as may be used in exemplary embodiments. The garment 38 including the dosimeters 28 may have the dosimeters 28 arranged in a regular grid shaped pattern, or in another arrangement of dosimeters, and may exemplarily extend along multiple sides (e.g. anterior, posterior, left and right oblique) of the patient. In an exemplary embodiment, use of the garment 38 with the dosimeters 28 provides a compromise of improved conformity to the patient's body, more closely resembling the patient models as described in further detail herein than other 2D dosimeter configurations while providing ease of donning and doffing the sensors for a large number of sensors as compared to solutions in which the dosimeters are adhered directly to the skin of the patient. The dosimeters 28 may also be arranged in an irregular grid with e.g. more dosimeters where the body curves more and less dosimeters where the body is flatter, to improve the overall accuracy.

Figure 4:
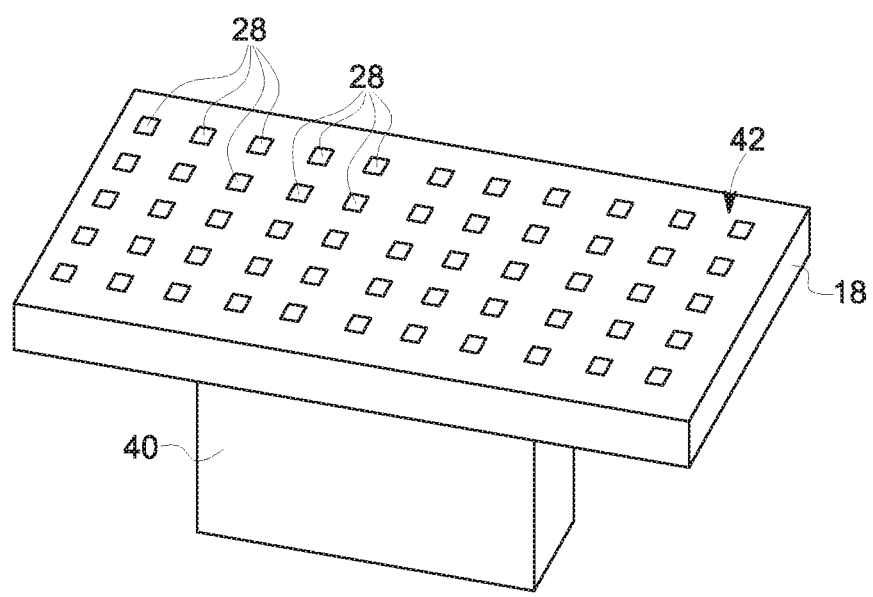
FIG. 4 depicts a still further exemplary embodiment in which a plurality of dosimeters are positioned within a tabletop.

FIG. 4 depicts a still further exemplary embodiment of the arrangement of the dosimeters 28. FIG. 4 depicts an exemplary embodiment of a tabletop 18 as may be used in connection with the medical imaging system 10 as depicted in FIG. 1. In an exemplary embodiment, the tabletop 18 is secured to a table base 40. The table base 40 is operable to move the tabletop 18 in multiple degrees of freedom to position the patient P (FIG. 1) relative to the X-ray source 14 and exemplarily the C-arm 12. The tabletop 18 includes a table surface 42 which may be configured to support the patient thereon. In the embodiment depicted in FIG. 4, the dosimeters 28 are positioned on the table surface 42. In an embodiment, a plurality of dosimeters 28 are positioned in a grid pattern on the table surface 42. In another embodiment, a single dosimeter 28 is positioned on the table surface 42. The dosimeters 28 may exemplarily be integrated into the table surface 42 while in another embodiment, the dosimeters may be exemplarily positioned in a cover or separate component that is laid across the table surface 42. While FIG. 4 depicts a plurality of small dosimeters 28, another embodiment may place a small number (e.g. one) large surface area dosimeter e.g. a radio reactive film over the table surface 42. In exemplary embodiments, a configuration in which the dosimeters are associated with a table surface 42 of the tabletop 18, may facilitate ease of use in placing the dosimeters in relation to the patient, while may further improve communication of the measured radiation dose, for example by leveraging the communicative connections already present in the tabletop 18 or communicative connects as may be associated therewith.

As previously described, the dosimeters may exemplarily be implemented in analog or digital embodiments. In still further exemplary embodiments, the radiation dose as measured by the dosimeter may be read from the dosimeters at varying sampling frequencies. In an exemplary embodiment, an analog film based dosimeter may be collected and read by a reading device which exemplarily detects and translate a color change of the film for change in another property due to radiation exposure and translates this into a dose measurement. This sampling frequency may also occur in embodiments which use digital dosimeters wherein the measured dose is only read from the dosimeter after the imaging procedure is completed. In other embodiments, the measured dose from the dosimeter (e.g. digital dosimeter) at any of a variety of sampling frequencies. In such embodiment, wired or wireless communicative connections between the dosimeter and the processing unit 26 enable the measured dose to be read from each of the dosimeters at periodic intervals (e.g. five minutes, one minute, or 30 seconds) or at increasing frequencies up to real-time or near real-time reading of radiation doses measured by the dosimeters. As described in further detail herein, the frequency of dose measurements reported to the system may result in different ways in which the estimated dose is calculated and reported.

In embodiments, registration between the actual locations of the dosimeters 28 on the patient model (as exemplarily depicted in FIG. 2) is needed to accurately estimate the patient dose during an imaging procedure as well as to accumulate radiation dose experienced by the patient plurality of imaging procedures.

As previously described, registration of the dosimeter locations and the patient model can be facilitated by user input of particular dosimeter locations, standard dosimeter locations on the patient to which dosimeters are secured and those locations incorporated into the patient models as well as the use of a locating system, for example a camera or set of cameras 30 to capture one or more images of the patient and the dosimeters in order to locate the dosimeter positions in the model of the patient as well as to improve registration of the X-ray source and the X-ray beam 34 in relation to the patient model 32. It will be recognized that other registration or location system including, but not limited to WIFI, electromagnetic, infrared, optical, ultrasound, or other location identification systems may be used for these purposes as well.

Exemplary embodiments of the medical imaging system as described herein combine patient modeling with dosimeter direct measurement for improved procedure and cumulative radiation dose estimation. Cumulative dose estimations are exemplarily provided by using a patient model and an X-ray beam model to produce a dose estimation model, exemplary embodiments of which will be described in further detail herein. In disclosed embodiments, dose measurements as provided by the one or more dosimeters as described above, is incorporated into the dose estimation models.

The systems and methods as disclosed herein may be used to improve the accuracy of the estimated doses intra-procedure as well as the estimation of cumulative radiation dose received by the patient by successive imaging procedures. The systems and methods as described herein do so by improving upon dose estimation models.

Dose estimation models create a geometric model of the patient. The patient may be modeled as a cylinder, an elliptical cylinder, or a combination of a sphere (or spheroid) (e.g. to represent a head) and a cylinder or an elliptical cylinder to represent the body. It will be recognized that other more complex shapes and/or surfaces may be used to model the patient body. In examples, the models may exemplarily be more anthropomorphic in shape than the geometric embodiments described above. In still further examples, the patient may be modeled based upon previous images of the patient's body using e.g. CT, MRI, or other imaging techniques to produce a 3D model.

In an exemplary embodiment, a 3D model can be approximated by a cylindrical shape enveloping the patient. The shape of the 3D model can be optimized by acquisition of patient contours or using conventional segmenting and reconstructing techniques from a plurality of acquired 2D images of the patient. In an embodiment, this may be performed using the digital camera or set of cameras 30 or by known X-ray imaging techniques available by operation of the X-ray source 14 and the detector 16. In an embodiment, the 3D model may also depend on variations in density of the different constituent parts of the patient. The processing may identify, in a 3D model, different elements or organs of the body of the patient (e.g. bone, flesh, heart, liver, and/or lungs) and embodiments may take into account the variations in the density of the different elements forming the body of the subject and is not limited to models reduced to simple geometric shapes having homogeneous densities. In still further embodiments, the patient may also be modelled by other shapes, including, but not limited to shapes selected from a library of known anthropomorphic shapes or from images or image data from a direct scan of the patient 3D surface that may have been taken prior to having the patient laid on the tabletop 18.

In an embodiment, the 3D model of the patient is stored in the storage unit 22 of the medical imaging system 10 in the form of an envelope of the model that assumes the shape of a mesh, each region of the mesh being defined by a plurality of vertices. The vertices correspond to the X-ray emission field for a current position of the X-ray source.

This mesh may correspond to sampling of the envelope of the 3D patient model in relation to the position of the X-ray source. Dose values for each region of the patient model are determined depending upon one or more parameters including, but not limited to air kerma, dependent upon exposure and the X-ray beam; the quantity of dose absorbed by the skin; the backscattering coefficient which may be seen as an X-ray filtering effect; and the coefficient of dose entry into the patient.

In an embodiment, for each dose value, in addition to the above-mentioned parameters, the geometry associated with each exposure is taken into account, for example the following parameters of the medical imaging system 10: the emission characteristics (voltage in kV, intensity in mA, filtrations in thickness unit); the properties of the emission tube; and the emitted focal spot size.

In an exemplary embodiment, for each position of the X-ray source, a region of the patient model exposed by the X-ray source at that position is determined and the dose value measured for that position is associated therewith. The distribution of the dose on the envelope of the model of the patient may be dependent upon the position of the model within a 3D region exposed by the X-ray source. The distribution of the dose can be made in 2D and/or 3D surfaces of the model envelope.

In a still further exemplary embodiment, the patient envelope can be modeled as a set of super-ellipses composed of a bottom (b) super-ellipse and a top (t) super-ellipse in order to take into account the different radii of the patient outer shape and may be defined as:

$$1 = \left(\frac{x + b_b/(b_b + b_t)}{h \times b_{b,t}}\right)^{n_{b,t}} + \left(\frac{y}{a_{b,t} \times w/2}\right)^{m_{b,t}} \quad (1)$$

The parameters $b_{b,t}$ and $a_{b,t}$ are, respectively, the semi-diameters of the curve in the $X_t$ and $Y_t$ directions. The parameters $n_{b,t}$ and $m_{b,t}$ act as the "squareness" parameters in the $X_t$ and $Y_t$ directions, respectively. In an exemplary embodiment, the value w is dependent upon the patient BMI (Body Mass Index) to better match the patient thoracic width. With the use of this equation, a patient body envelope model that generally shows improved correspondence to a patient lying in a supine position on a flat table can be provided.

A head envelope can be modeled, taking into account the three body planes (sagittal, transverse, and coronal) of the head in the following equation:

$$1 = \left(\frac{x}{\alpha}\right)^m + \left(\frac{y}{\beta}\right)^n + \left(\frac{z}{\gamma}\right)^o \quad (2)$$

The parameters α (alpha) β (beta) and γ (gamma) are, respectively, the dimensions of the head corresponding to the intersection axes of the coronal and transverse planes, transverse and sagittal planes, and the sagittal and coronal planes.

Figure 5:
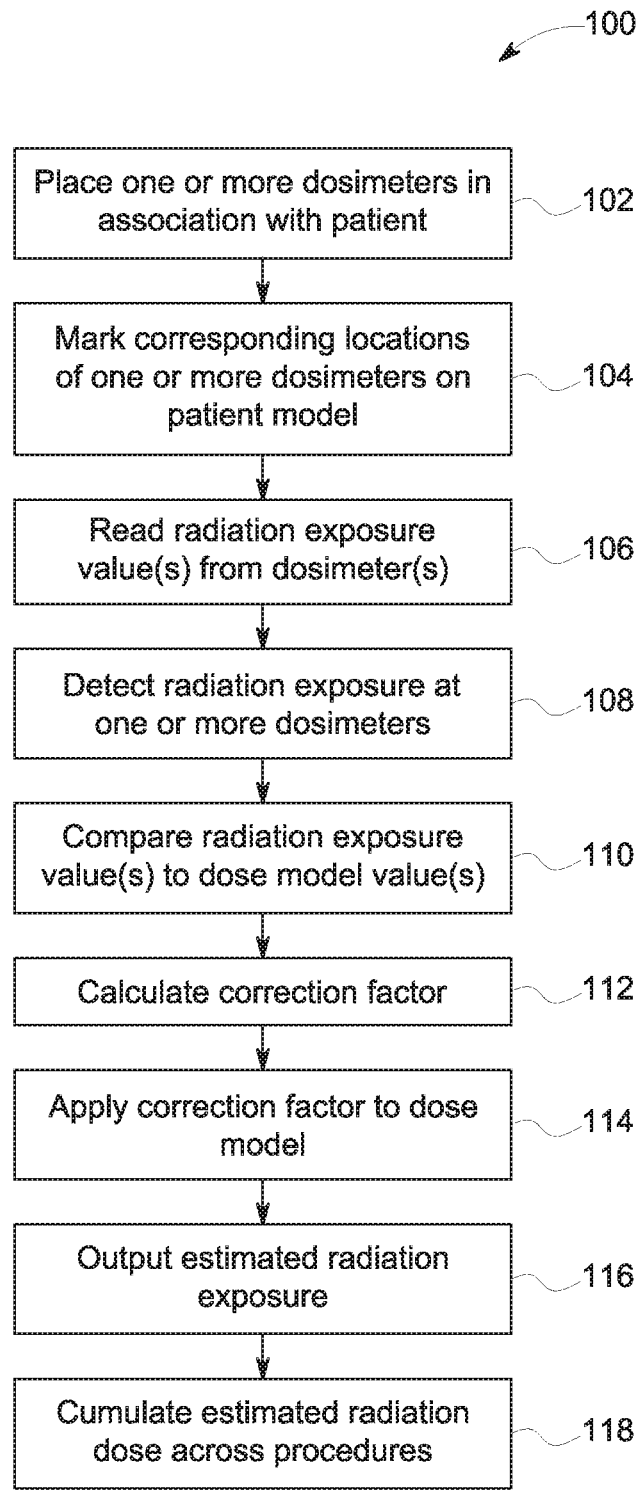
FIG. 5 a flow chart that depicts an exemplary embodiment of a method of estimating radiation dose.

FIG. 5 is a flow chart that depicts an exemplary embodiment of a method 100 of estimating radiation dose. At 102, one or more dosimeters are placed in association with a patient. As previously described, the dosimeters may exemplarily be analog or digital dosimeters and may be secured to the skin of the patient, secured to a garment worn by the patient, or positioned on the table upon which the patient rests during the imaging procedure.

At 104, corresponding locations of the one or more dosimeters placed on the patient are marked on a patient body model selected of created for the patient. As previously explained, the patient body model may be cylindrical or anthropomorphic and may include a variety of geometrical modeling techniques. In still further exemplary embodiments, the patient body model may be modeled from a current or a previously imaging procedure, including, but not limited to X-ray and/or CT images of the patient. The corresponding locations of the one or more dosimeters may be marked on the patient model in a variety of ways. In one embodiment, the positions of the dosimeters are predefined in a set of sensor locations incorporated into the patient body model. These locations may be predefined. For example, as predefined anatomical locations (e.g. L5 vertebra, shoulder blades, sternum, ribs, outer most lateral positions of the chest etc.). When the clinician places the dosimeters at 102 the clinician places the dosimeters in association to the patient according to the predefined anatomical location in another exemplary embodiment, the dosimeters may have been freely placed by a clinician and the location of each dosimeters is defined, for example by measurements relative to anatomical landmarks so that the positions of the dosimeters may be input to the patient body model. In a still exemplary embodiment, if the number and/or spatial relationship of the dosimeters is fixed and/or known, for example the dosimeters are secured to a garment worn by the patient or are located in the table upon which the patient rests location of one identified dosimeter or a registration features associated with the dosimeters may be used to input the locations of the known array of dosimeters. In an exemplary embodiment, a model of the garment worn by the patient, along with the array of dosimeters located in the garment may be provided and the clinician inputs a location of a registration feature of guide of the garment relative to the patient body model and the array of dosimeters are positioned on the model accordingly.

In a still further exemplary embodiment wherein the dosimeters are located in the table upon which the patient rests, the patient may be registered to the table, for example using a digital camera to acquire the shape and/or envelope of the patient's body relative to the table and the array of dosimeters located on the table. By capturing this patient body envelope, for example through edge detection processing of the digital image, the locations of the dosimeters in the table relative to the patient body model may be marked.

Next, at 106 radiation is detected at one or more dosimeters. As previously disclosed, embodiments of the systems and methods as disclosed herein vary in the frequency at which the dose value from the dosimeters are read and the estimate of radiation exposure of the patient is determined. Therefore, reading the radiation exposure values from the one or more dosimeters at 106 may exemplarily occur after completion of the imaging procedure, or may occur at varying frequencies in communicatively connected embodiments that provide periodic and/or real-time updates to the radiation exposure values determined by the dosimeters. In an exemplary embodiment, the radiation exposure values may be read and analog dosimeters by an image capture system which translates the analog change in a property of the dosimeters (e.g. color) to a value representative of the radiation exposure. In exemplary embodiments using digital dosimeters, the radiation exposure values determined by the dosimeters may be read by a communicatively connected processing unit. The communicative connection may be a wired or wireless connection. In still further exemplary embodiments the dosimeters may be read after the completion of the imaging procedure for example by reading an RFID tag to which the dosimeters write the determined radiation exposure value or by a communicative connection either through a communication port (e.g. USB port, BLUETOOTH, ZIGBEE, or other wireless or near field communication platforms).

If a radiographic imaging procedure has occurred, and the dosimeters properly positioned relative to the imaging procedure, one or more of the radiation exposure values read from the one or more dosimeters will be detected as having been subjected to radiation exposure. If one or more dosimeters have experienced radiation exposure, it can be assumed that the patient has as well and the radiation dose can be estimated and accumulated for the patient. In an exemplary embodiment, only those dosimeters which register radiation exposure and have a non-zero radiation exposure value need be used in the estimation of radiation dose. While in other embodiments, the radiation exposure value from each known dosimeter is used, including those dosimeters with a zero dose value in order to more accurately represent those areas of the patient which were not subjected to radiation dose.

At 110, the radiation exposure values are compared to a dose model value based upon the patient body model and the characteristic of the radiation as may be input by a clinician. As previously described, the dose model incorporates the position of the X-ray source relative to the patient, as well as the strength of the X-ray beam, shape of the X-ray beam, the angulation of the X-ray source, and/or the duration of the image procedure, as well as other exemplary imaging settings to estimate the radiation exposure at each point of the patient body model therefore, at 110 the measured radiation exposure values from the dosimeters are compared to the dose model values at the same locations as each of the dosimeters. At 112 at least one correction factor is calculated from this comparison between the measured radiation values and the resulting values from the dose model. At 114 the calculated at least one correction factor is applied to the dose model and new estimations of the radiation dose are calculated. In an exemplary embodiment, a correction factor is calculated for each of the radiation exposure values obtained from each of the dosimeters. Methods 200 and 300 as described in further detail herein presents two exemplary embodiments of ways in which the at least one correction factor may be calculated and applied to the dose model.

Figure 6:
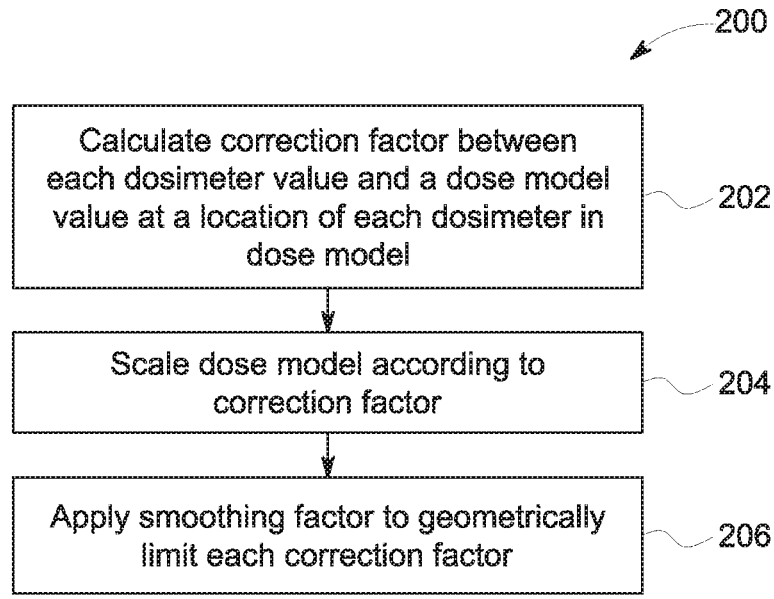
FIG. 6 is a flow chart that depicts an exemplary embodiment of a method of correcting dose mapping.

FIG. 6 depicts a first exemplary embodiment of a method 200 of correcting dose mapping. The method 200 begins at 202 wherein a correction factor is calculated between each dosimeters value and a dose model value at a location of each dosimeter in the dose model. Next, at 204 the at least one correction factor is used to scale the algorithm of the dose model according to the at least one correction factor. In an exemplary embodiment, the correction factor may be applied as a scaling value across all of the 3D dose models. In a non-limiting embodiment, the dose model may include a correction factor variable, which for example have a default value of 1.0. The at least one correction factor as calculated based upon the difference between the dosimeter value and the dose model value at the same location is used to update this variable with the new correction factor. In an exemplary embodiment wherein a single dosimeter is used, this correction may be applied across the entire dose model. In another exemplary embodiment, at 206 a smoothing factor may further be applied to the correction factor to geometrically limit the correction factor to an area about the location of the dosimeter underlying the correction factor. The smoothing factor may eventually diminish to the default value of the correction factor in the dose model based upon a distance, location, and direction of each point in the dose model from the location of the dosimeter from which the correction factor was calculated. In still further embodiments, such smoothing factor may be used in embodiments wherein the radiation exposure values from multiple dosimeters are used, resulting in different correction factors at different locations in the dose model. The smoothing factor may be applied to the correction factors based upon each of the dosimeter values, to account for the dosimeter value. The application of the correction factors to the surrounding estimation values in the dose model can be thus geometrically limited. Therefore, in an exemplary embodiment wherein the correction factors from multiple dosimeters values may be incorporated into points in the dose model located between locations in which dosimeter values were read.

It will be recognized that embodiments of the method 200 may exemplarily be used in association with embodiments with comparatively fewer dosimeters associated with the patient. The scaling approaches as described therein with respect to the method 200 may be used to meaningfully extend limited dose measurement values across the dose model. It will be recognized that still further embodiments of calculating the correction factor and scaling the dose model according to the correction factor may be implemented while remaining within the scope of the present disclosure. In a further non-limiting example, an average correction factor between the correction factors calculated at 202 or a weighted average based upon dosimeter location relative to either the patient and/or the X-ray source may be used to scale the dose model.

Figure 7:
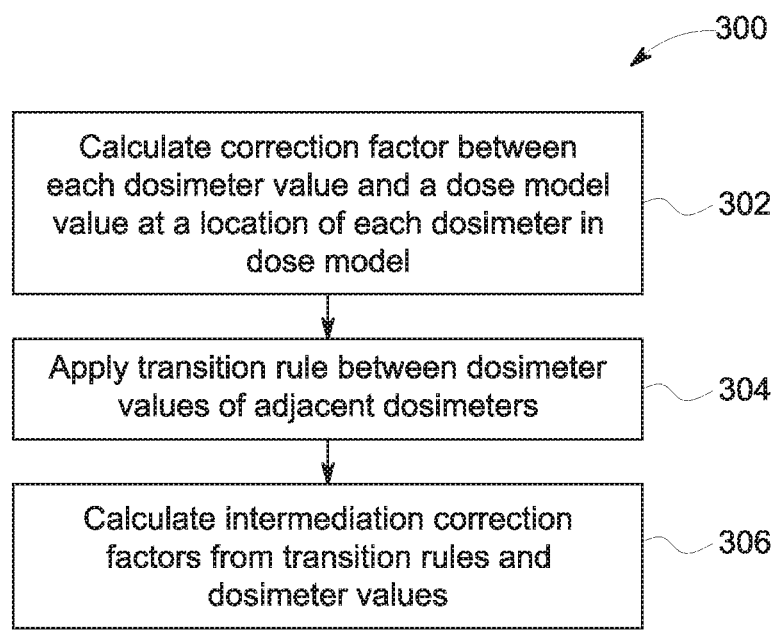
FIG. 7 is a flow chart that depicts another exemplary embodiment of a method of correcting dose mapping.

FIG. 7 is a flow chart that depicts an exemplary embodiment of a second method 300 of correcting dose mapping. The method 300 begins at 302 by calculating a correction factor between each dosimeter value and a dose model value at a location of each dosimeter in the dose model. In an exemplary embodiment, the method 300 may exemplarily be used in connection with embodiments in which a comparatively larger number of dosimeters are positioned relative to the patient, and for example positioned at regular intervals for example in an array of dosimeters associated with the patient either in a garment or in a table upon which the patient is resting. In such exemplary embodiments, the array of dosimeters provides a coarse matrix of dosimeter measurement values. In an exemplary embodiment because such embodiment provide a coarse matrix of measured dose values, these measured dose values are taken at face value and used in the resulting dose map and/or output of estimated radiation exposure. The correction factor calculated at 302 are therefore used to extrapolate and extend the measured dose values according to the underlying dose model to fill in the gap between the dose value measurements. This is exemplarily performed by applying at least one transition rule between the dosimeter values of adjacent dosimeters. The transition rules may exemplarily be based upon step functions, which may include a predefined step number and/or step side, a linear interpolation, or an exponential interpolation, or any other appropriate function. The transition rules may exemplarily be modeled in two dimensions and/or three dimensions in order to geometrically relate the position of the measured dosimeter values at the locations relative to the patient body model along the possibly complex shape of the patient body model between those locations. Additionally, in the example of an array of dosimeters, each dosimeter, for example in a rectangular array may be adjacent to eight other dosimeters and the gaps between the measurements of each of these dosimeters may be interrelated.

Exemplary embodiments of the transition rules may opt for a sharper transition, for example as provided by an exponential decay or a step wire function such as to better represent instances of sharp transition in dose as may occur between adjacent measured dose values of differing magnitudes.

At 306 intermediate correction factors are calculated from the application of the transition rules to the dosimeters values. The intermediation correction factors from 306 are used as the correction factors in the dose model to calculate the estimated radiation dose in the maps between the measured dose values according to the dose model.

Figure 8:
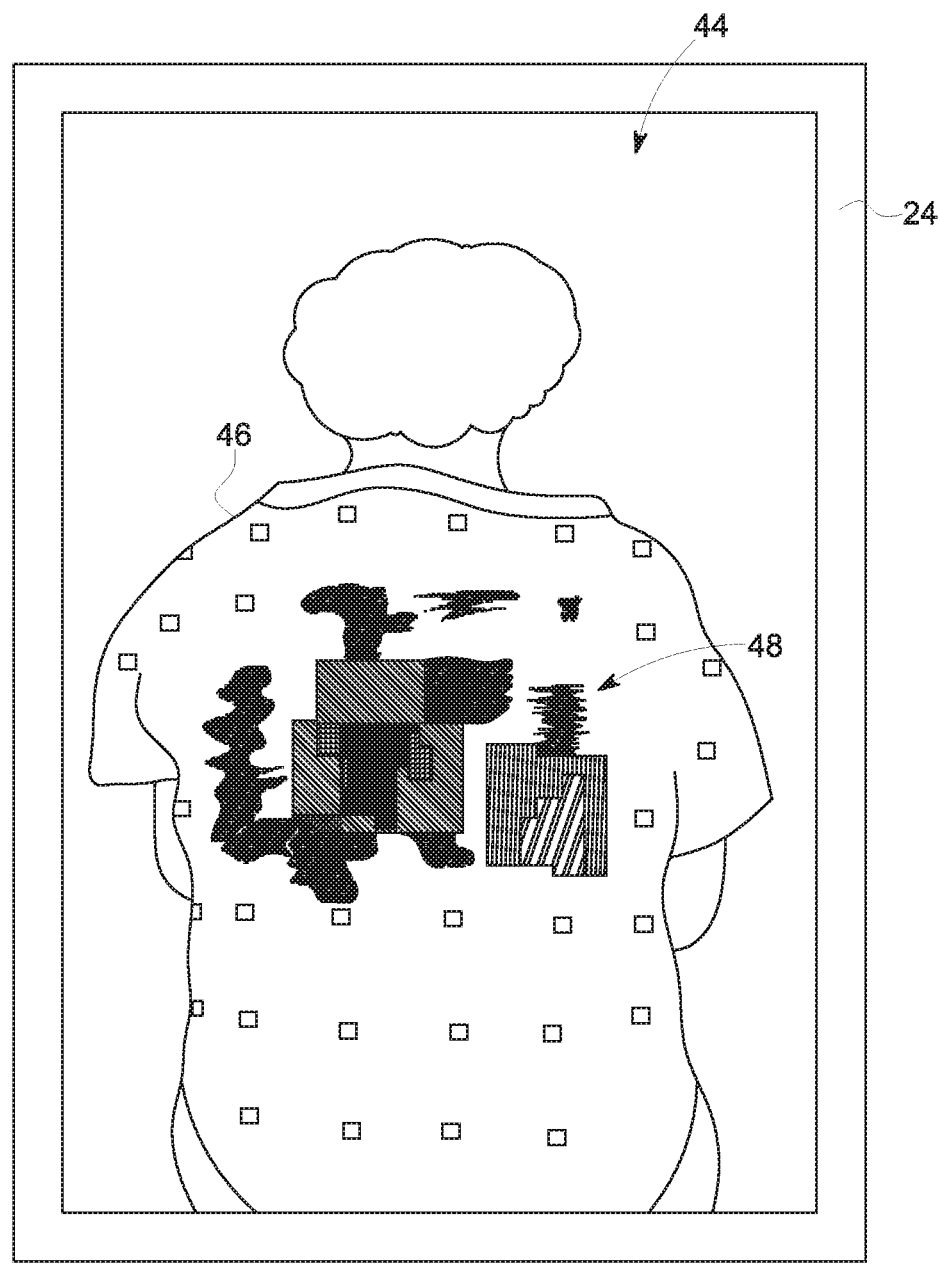
FIG. 8 depicts an exemplary embodiment of a graphical user interface with a graphical representation of a patient and a dose map.

Referring back to FIG. 5, the dose model with the correction factures is used to estimate the radiation dose to which the patient was exposed. This estimation of radiation exposure is output at 116. In an exemplary embodiment, the output of estimated radiation exposure is a dose map. A dose map graphically depicts the radiation exposure to various areas on the patient's body. FIG. 8 depicts a merely exemplary embodiment of a graphical user interface (GUI) 44 presented on a graphical display 24 which includes a graphical representation of a patient 46 and a dose map 48 shown in color of shade gradient indicative of radiation exposure at that point of the patient's body according to the dose model as improved in the manner as described above.

It will be recognized that in exemplary embodiments, if the dosimeters are read after the imaging procedure, that the estimated radiation exposure exemplarily presented on the dose map is representative of the radiation exposure from the entire imaging procedure. In another embodiment wherein the dosimeters are periodically read during the imaging procedure, the dose map may be updated with each reading of the dosimeters to reflect the progressive accumulation of radiation exposure by the skin of the patient during the imaging procedure. After the radiation exposure for the imaging procedure is estimated, this estimation may be saved in a computer readable medium, for example in a patient electronic medical record (EMR). Such radiation exposure information may be stored at the computer storage 22 or exemplarily at another local or remote location.

In an exemplary embodiment, at 118 estimated radiation does across multiple imaging procedures are accumulated for the patient. Because the dosimeters are associated with the patient and are located on the patient body model, the location of the estimated radiation exposure is more accurately located in the dose model for each imaging procedure and the total accumulated radiation dose across multiple imaging procedures can be additively combined to present an estimation of the total radiation exposure received by the patient across all monitored imaging procedures. It will be recognized that in other embodiments, such estimations of accumulated radiation dose may not necessarily be limited to only the imaging procedures as described herein, but may also estimate radiation dose received by the patient from other types of imaging, including, but not limited to X-ray and/or CT or from sources of therapeutic radiation exposure may also be accumulated by use of the methods as disclosed herein.

In exemplary embodiments, such accumulation of the estimated radiation dose across multiple imaging procedures may be performed by accessing previously stored dose estimates from previous imaging procedures. The dose estimates from the previous imaging procedures may be combined with the radiation dose estimate from the current procedure. In an exemplary embodiment, the total accumulated dose may be an additive combination of all of the estimated radiation doses. In an embodiment, only radiation dose estimates from procedures within a predetermined temporal length (e.g. four weeks) from the current radiation dose are used. In a still further embodiment, the accumulation of the estimated radiation dose weights the estimated radiation dose based upon an elapsed time since the imaging procedure, with the radiation doses from more recent imaging procedures being given more weight.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for estimation of radiation dose of a medical imaging system, the system comprising:
   a dosimeter adapted to be associated with a patient; and
   a processing unit that obtains at least one dose model comprising a patient model, receives at least one radiation exposure value from the dosimeter, marks a location of the dosimeter on the patient model, estimates the radiation exposure of the patient during an imaging procedure according to the dose model, calculates at least one correction value based upon the estimated radiation exposure of the patient according to the dose model and the at least one radiation exposure value received from the dosimeter, applies the at least one correction factor to the dose model and produces a refined estimation of radiation exposure of the patient based upon the at least one correction factor and the dose model.

2. The system of claim 1, further comprising an X-ray source configured to generate an X-ray beam in an imaging procedure in the direction of the dosimeter.

3. The system of claim 1, wherein the dosimeter is an analog dosimeter.

4. The system of claim 1, wherein the dosimeter is a digital dosimeter communicatively connected to the processing unit and the processing unit reads a radiation exposure value from the digital dosimeter at a sampling interval.

5. The system of claim 1, further comprising a plurality of dosimeters including the dosimeter, the plurality of dosimeters arranged in an array and integrated into a garment configured to be worn by the patient.

6. The system of claim 1, further comprising a plurality of dosimeters including the dosimeter, the plurality of dosimeters arranged in an array and associated with a table configured to support the patient during the imaging procedure.

7. The system of claim 1, further comprising at least one digital camera communicatively connected to the processing unit, wherein at least one image captured by the at least one digital camera is used by the processing unit to mark the location of the dosimeter on the patient model.

8. The system of claim 1, wherein the refined estimation of radiation exposure of the patient is visually presented as a dose map on a graphical display operated by the processing unit.

9. The system of claim 1, wherein the processor applies the at least one correction factor to the dose model by scaling the dose model according to the at least one correction factor.

10. The system of claim 1, further comprising:
    a plurality of dosimeters including the dosimeter, wherein a location of each of the dosimeters of the plurality is marked on the patient model and the processing unit receives a plurality of radiation exposure values from the plurality of dosimeters;
    wherein the processing unit calculates a plurality of dose model values and calculates a plurality of initial correction factors between each of the radiation exposure values from the plurality of dosimeters and a dose model value of the plurality of dose model values at a corresponding location in the patient model, the processing unit applies a transition rule between radiation exposure values of adjacent dosimeters and calculates intermediation correction factors based upon the transition rule and the radiation exposure values; and
    wherein the refined estimation of radiation exposure of the patient comprises the radiation exposure values from the plurality of dosimeters and the dose model values corrected by the intermediation correction factors for locations on the dose model between the locations of the radiation exposure values.

11. A method of estimating radiation dose, the method comprising:
    obtaining a patient model;
    marking a location of at least one radiation exposure value measurement on the patient model;
    obtaining at a processor at least one radiation exposure value from a radiation exposure event;

estimating a radiation exposure of the patient during the radiation exposure event with a dose model comprising the patient model to produce at least one dose model value;

calculating at least one correction factor based upon the at least one radiation exposure value and the at least one dose model value;

applying the at least one correction factor to the dose model; and producing a refined estimation of radiation exposure of the patient based upon the at least one correction factor and the dose model.

12. The method of claim 11, further comprising outputting the estimated radiation exposure in a dose map visually presented on a graphical display.

13. The method of claim 11, further comprising:

estimating the radiation exposure of the patient for a plurality of radiation exposure events; and cumulating the estimated radiation exposure from the plurality of radiation exposure events to produce a total estimated radiation exposure by the patient.

14. The method of claim 11, Further comprising comparing the at least one radiation exposure value to the at least one dose model value, wherein the correction factor value is based upon the comparison between the at least one radiation exposure value and the at least one dose model value.

15. The method of claim 11, further comprising positioning a plurality of dosimeters in association with the patient and obtaining at the processor a plurality of radiation exposure values, including the at least one radiation exposure value, from the plurality of dosimeters.

16. The method of claim 15, further comprising reading radiation exposure values from the plurality of dosimeters during the radiation exposure event to obtain the radiation exposure values.

17. The method of claim 11, further comprising:

wherein the location the at least one radiation exposure value measurement marked on the patient model comprises a plurality of locations of radiation exposure value measurements;

wherein at least one radiation exposure value is a plurality of radiation exposure values obtained by the processor from a plurality of locations marked on the patient model;

wherein the at least one dose model value is a plurality of dose model values from the same locations on the dose model as the plurality of locations marked on the patient model; and wherein calculating the at least one correction value comprises calculating a plurality of correction factors between each of the radiation exposure values of the plurality of radiation exposure values and a dose model value of the plurality of dose model values at a corresponding location in the patient model.

18. The method of claim 17, further comprising scaling the dose model with the plurality of correction factors, wherein the radiation exposure of the patient is estimated based upon the dose model scaled by the plurality of correction factors.

19. The method of claim 18, further comprising applying a smoothing factor to each of the plurality of correction factors to geometrically limit each correction factor of the plurality of correction factors.

20. The method of claim 17, further comprising:

applying a transition rule between radiation exposure values of adjacent dosimeters; and calculating intermediation correction factors based upon the transition rules and the radiation exposure values;

wherein the estimating the radiation exposure of the patient comprises the radiation exposure values and the dose model values corrected by the intermediation correction factors for locations on the dose model between the locations of the radiation exposure values.

* * * * *